United States Patent [19]

Jolles et al.

[11] Patent Number: 4,716,151

[45] Date of Patent: Dec. 29, 1987

[54] TRIPEPTIDES AND THEIR USE

[75] Inventors: Pierre Jolles, Paris; Daniele Migliore-Samour, Le Kremlin-Bicetre; Fabienne Parker, St Maur-des-Fosses, all of France

[73] Assignee: Rhone-Poulenc Sante, Courbevoie, France

[21] Appl. No.: 765,536

[22] Filed: Aug. 14, 1985

[30] Foreign Application Priority Data

Aug. 16, 1984 [FR] France ................................ 84 12853

[51] Int. Cl.$^4$ ......................... A61K 37/02; C07K 5/08
[52] U.S. Cl. ..................................... 514/18; 530/331
[58] Field of Search ........................... 514/18; 530/331

[56] References Cited

FOREIGN PATENT DOCUMENTS

| | | |
|---|---|---|
| 1046441 | 1/1979 | Canada . |
| 1497536 | 10/1967 | France . |
| 1158721 | 7/1969 | United Kingdom . |
| 1158722 | 7/1969 | United Kingdom . |
| 1158723 | 7/1969 | United Kingdom . |
| 1158724 | 7/1969 | United Kingdom . |
| 1158725 | 7/1969 | United Kingdom . |
| 1158726 | 7/1969 | United Kingdom . |
| 1158727 | 7/1969 | United Kingdom . |

OTHER PUBLICATIONS

Chem. Abstr., vol. 95, (1981), 169747.
Chem. Abstr., vol. 94, (1981), 1489.
Chem. Abstr., vol. 101, (1984), 211716.
Virology 129, 357–368, (1983).
Chem. Abstr., vol. 98, (1983), 122350.
Chem. Abstr., vol. 71, (1969), 39379.
Chem. Abstr., vol. 97, (1982), 155609.
Chem. Abstr., vol. 103, (1985), 115376.
Chem. Abstr., vol. 97, (1982), 88070.
Chem. Abstr., vol. 104, (1986), 162102.
Chem. Abstr., vol. 103, (1985), 2597.
Chem. Abstr., vol. 103, (1985), 105313.
Chem. Abstr., vol. 100, (1984), 34806.
Chem. Abstr., vol. 104, (1986), 141471.
Chem. Abstr., vol. 77, (1972), 19993.
Chem. Abstr., vol. 102, (1985), 2878.
Chem. Abstr., vol. 103, (1985), 22912w.
Chem. Abstr., vol. 103, (1985), 119106.
Chem. Abstr., vol. 89, (1978), 44249.
Chem. Abstr., vol. 87, (1977), 184942.
Chem. Abstr., vol. 104, (1986), 15379.
Chem. Abstr., vol. 99, (1983), 22912.
Chem. Abstr., vol. 100, (1984), 121604.
Chem. Abstr., vol. 101, (1984), 171711.
J. C. S. Perkin I, "Methods of Peptide Sequencing, Part II. Cyclisation of N-2-Amino-6-nitrophenyl and N-3-Amino-2-Pyridyl Derivatives of Amino acids and Peptides", pp. 1424–1427, dated Jan. 23rd, 1975.

*Primary Examiner*—Delbert R. Phillips
*Attorney, Agent, or Firm*—Stevens, Davis, Miller & Mosher

[57] ABSTRACT

Tripeptides composed of the amino acids glycine, leucine, and phenylalanine or tyrosine obtainable by fractionation of hydrolysis products of human casein or by direct synthesis can be used as immunostimulants.

4 Claims, 2 Drawing Figures

TRIPEPTIDES AND THEIR USE

The present invention relates to immunostimulants and their use.

In European Patent EP No. 0049666 (INSERM, published Apr. 14, 1982), corresponding to U.S. Pat. No. 4462990 and Japanese Patent Application No. 81/503192, there were described biologically active substances obtained by fractionation of enzyme hydrolysates of human casein, and the compositions which contain them.

More especially, the fractionation on a Sephadex G-50 column of the water-soluble fraction originating from the treatment of delipidised, solubilised human casein with trypsin for 24 hours at 37° C. yields three biologically active fractions designated "substances IV, V and VI", among which "substance V", when purified on a DEAE Sephadex A-25 column, yields the neutral substance known as "MJH 24" on elution with a buffer solution at pH in the region of 8, and then the substances of an acidic nature known as "MJH 63" and "MJH 65" on elution with a buffer solution at pH in the region of 3.5.

It has now been found that purification of the substance "MJH 65" by filtration on Sephadex G-15, and then by high performance liquid chromatography (HPLC) after desalification, enables a tripeptide to be isolated, the structure of which corresponds to the sequence:

Gly-Leu-Phe          (I)

The structure of the tripeptide of formula (I) was determined:
  by complete hydrolysis with 6N hydrochloric acid at 110° C. for 18 hours,
  by dansylation to determine the nature of the N-terminal amino acid,
  by the action of carboxypeptidase A
  by automatic degradation with a BECKMANN sequenator model 890 C.

The tripeptide of formula (I) and the similar tripeptides which are a combination of three amino acids, viz. glycine, leucine and phenylalanine or tyrosine, which can be readily synthesised by application of the usual methods used in peptide chemistry (e.g. according to the process described in French Patent FR No. 1,497,536), have noteworthy immunostimulant properties. In the new tripeptides, one or two of the three amino acid residues is derived from glycine or leucine, and two of the three residues may be derived from the same amino-acid.

DETAILED DESCRIPTION OF THIS INVENTION

Figure 1:
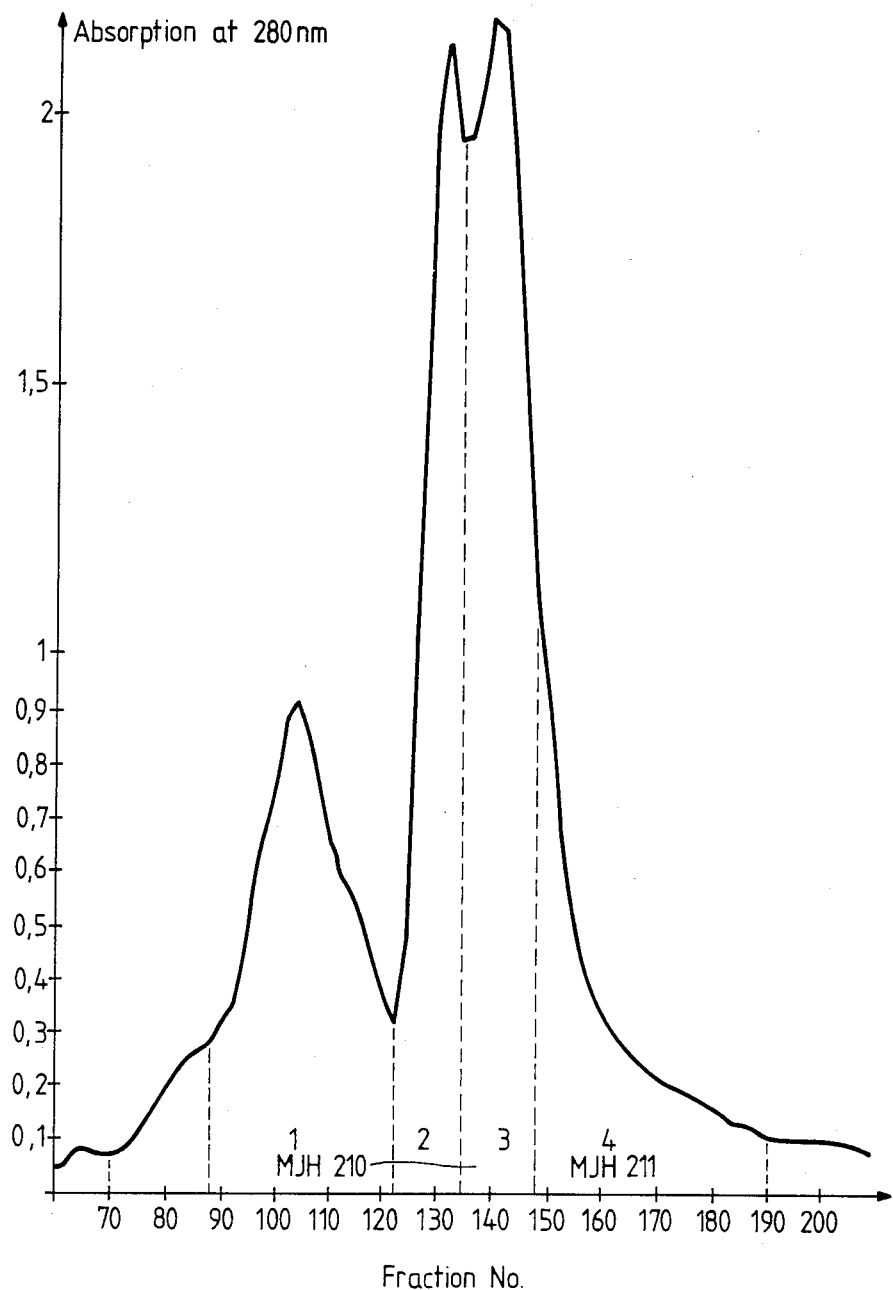
FIG. 1 is a curve illustrating the separation of fractions MJH 210 and MJH 211 from substance MJH 65.

More especially, the tripeptide of formula (I), and the aforesaid similar tripeptides, have been shown to be active at concentrations between $10^{-5}$ and $10^{-7}$M in the test of increase of the number of phagocytic macrophages according to the technique of J. Michl et al, J. exp. Med., 144, 1465 (1976).

The present invention also provides pharmaceutical compositions which contain at least one tripeptide according to the invention, in combination with one or more diluents or excipients which are compatible and pharmaceutically acceptable. These compositions can be used to promote and increase the removal of infectious agents. As non-specific immunostimulants promoting immunity against infection, the tripeptides according to the invention can be administered at doses between 0.1 and 100 mg/kg parenterally (intravenously, subcutaneously or intramuscularly), intranasally, orally or rectally.

As solid compositions for oral administration, tablets, pills, powders or granules can be used. In these compositions, the active product is mixed with one or more diluents such as sucrose, lactose or starch. These compositions can also contain substances other than the diluents, e.g. a lubricant such as magnesium stearate.

As liquid compositions for oral administration, pharmaceutically acceptable emulsions, solutions, suspensions, syrups or elixirs containing inert diluents, such as water or liquid paraffin, can be used. These compositions can contain substances other than the diluents, e.g. wetting, sweetening or flavouring products.

The compositions for parenteral administration can be sterile aqueous solutions, or they can be suspensions or emulsions. As a vehicle, polyethylene glycol, a polypropylene glycol, vegetable oils, especially olive oil, and injectable organic esters, e.g. ethyl oleate, can be employed. These compositions can also contain adjuvants, especially wetting agents, emulsifiers or dispersants.

Sterilisation can be performed in several ways, e.g. by means of a bacteriological filter, by incorporating sterilising agents in the composition or by heating. They can also be prepared in the form of solid compositions, made sterile, e.g., by irradiation, which can be dissolved in sterile water or dispersed in any other injectable sterile medium, optionally at the time of use.

The compositions for intranasal administration can be sterile aqueous solutions, or they can be suspensions or emulsions, which can optionally be combined with a compatible propellant.

The compositions for rectal administration are suppositories which can contain, in addition to the active product, excipients such as cocoa butter or a semi-synthetic glyceride.

The examples which follow illustrate the isolation of the tripeptide of formula I and of the compositions which contain it.

EXAMPLE 1

Substance "MJH 65", the isolation of which is described in Example 2 of European Patent EP No. 0049666 is purified by filtration on a Sephadex G-15 column. A column 120 cm high and 1.2 cm in diameter is used. Elution is with 10% strength acetic acid, collecting 0.6−cc fractions with a flow rate of 9 cc/hour.

The elution diagram is shown in FIG. 1, in which the fraction number is plotted as abscissa and the absorption at 280 nm as ordinates.

The fraction "MJH 210", eluted between 81.6 and 88.8 cc (fractions 136 to 148) and the fraction "MJH 211", eluted between 88.9 and 114 cc (fractions 149 to 190), are thus collected.

The fraction "MJH 210" is desalified on a Dowex 50×4 column 14 cm high and 1.4 cm in diameter.

The elution is performed collecting 4.3—cc fractions with a flow rate of 24 cc/hour, using as eluents 0.05N hydrochloric acid (100 cc), water (100 cc) and then 2M ammonia solution.

A fraction "3", eluted between 34.4 and 81.7 cc with 2M ammonia solution, is thus collected.

This fraction "3" is purified by reverse phase HPLC on a semi-preparative column (Bondapack $C_{18}-\mu$ column, Waters), the length of which is 30 cm and the diameter of which 7.8 mm. 0.5—cc fractions are collected, the elution rate being 1 cc/minute.

At the beginning, the column is buffered with 0.1% strength trifluoroacetic acid (eluant A).

An eluant is prepared containing trifluoroacetic acid (0.1% by volume) and acetonitrile (70% by volume) in water (eluant B).

The elution is performed using a linear elution gradient, proceeding according to the following Table:

| Time (minutes) | Eluant A | Eluant B |
| --- | --- | --- |
| 0 | 100 | 0 |
| 10 | 100 | 0 |
| 110 | 50 | 50 |
| 140 | 0 | 100 |

The elution is followed by taking readings at 280 nm and by the fluorescence after reaction with fluorescamine at 490 nm.

Figure 2:
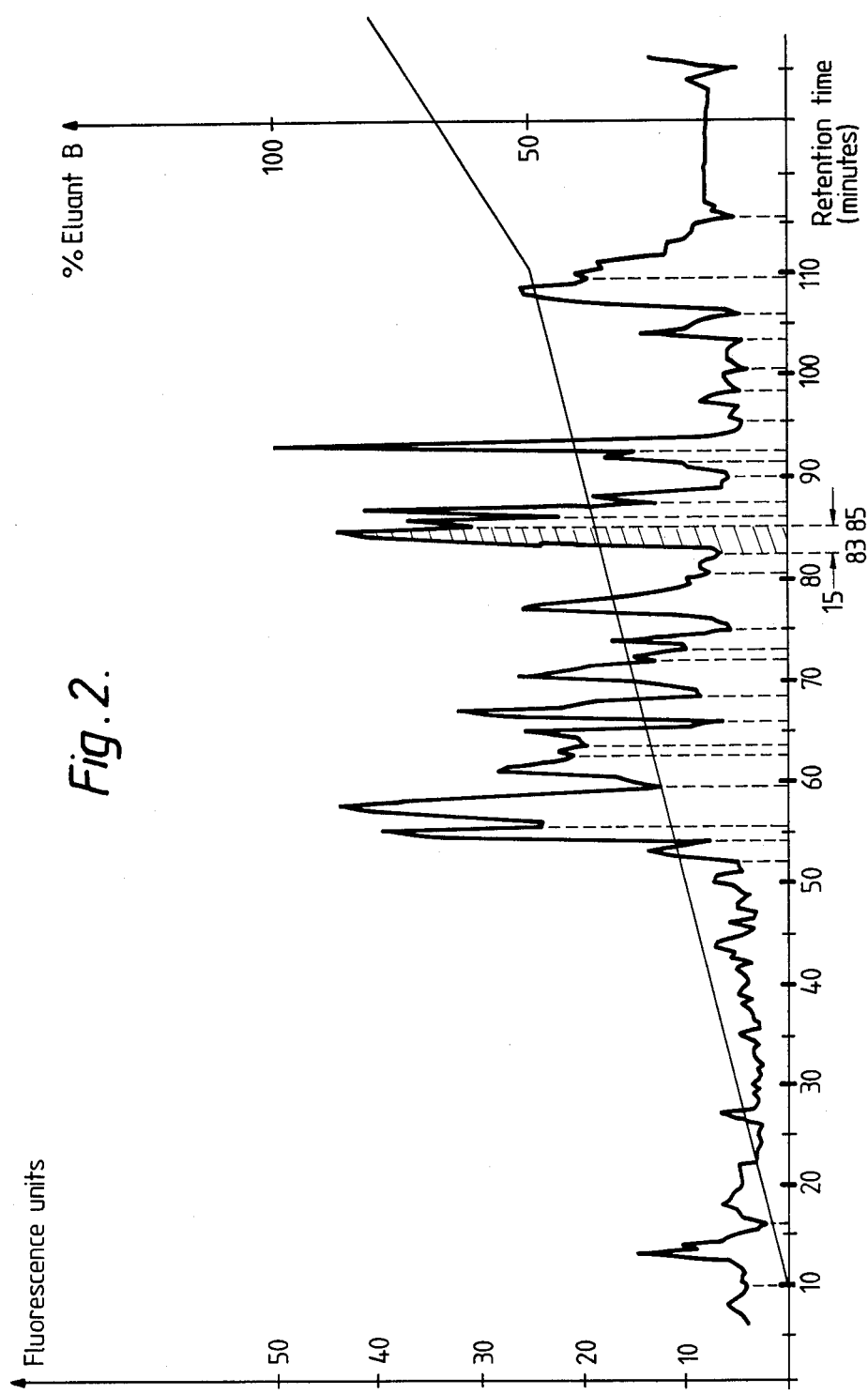
FIG. 2 is a curve illustrating the separation of pure tripeptide of formula (I).

The elution diagram is shown in FIG. 2.

The fraction No. 15, eluted between 83 and 85 minutes, contains the pure tripeptide of formula (I).

The structure of the tripeptide of formula (I) is determined:

by complete hydrolysis with 6N hydrochloric acid at 110° C. for 18 hours, which shows the presence of glycine (Gly)=1, Leucine (Leu)=1 and phenylalanine (Phe)=1, by dansylation in order to determine the nature of the N-terminal amino acid, which is glycine, by analysis with a Beckmann sequenator model 890 C, 0.1M Quadrol programme, with determination of the different stages by means of characterisation of the amino acid phenylthiohydantoin derivatives (determination by HPLC and visualisation on plates).

EXAMPLE 2

By applying the usual methods employed in peptide chemistry, the following tripeptides are prepared:

-Gly-Phe-Leu
-Leu-Gly-Phe
-Phe-Leu-Gly
-Leu-Phe-Gly
-Phe-Gly-Leu
-Gly-Tyr-Leu
-Leu-Gly-Tyr
-Tyr-Leu-Gly
-Leu-Tyr-Gly
-Tyr-Gly-Leu
-Gly-Leu-Tyr
-Leu-Leu-Tyr

EXAMPLE 3

There is prepared according to the usual technique a liquid composition which can be administered intravenously, having the following composition:
tripeptide of formula (I): 50 mg
injectable solvent: 5 cc.

We claim:

1. A pharmaceutical composition having immunostimulant activity comprising an effective amount of a tripeptide selected from the group consisting of Gly-Leu-Phe, Gly-Leu-Tyr and Gly-Phe-Leu in combination with one or more diluents or adjuvants which are compatible and pharmaceutically acceptable.

2. A pharmaceutical composition according to claim 1 comprising the tripeptide Gly-Leu-Phe in combination with one or more diluents which are compatible and pharmaceutically acceptable.

3. A method of stimulating the immune system in a subject which comprises administering to such subject an effective amount of a tripeptide selected from the group consisting of Gly-Leu-Phe, Gly-Leu-Tyr and Gly-Phe-Leu.

4. A method according to claim 3 in which an effective amount of the tripeptide Gly-Leu-Phe is administered to said subject.

* * * * *